(12) United States Patent
Hood et al.

(10) Patent No.: US 7,067,726 B2
(45) Date of Patent: Jun. 27, 2006

(54) COMMERCIAL PRODUCTION OF RECOMBINANT MANGANESE-DEPENDENT PEROXIDASE IN PLANTS

(75) Inventors: Elizabeth Hood, College Station, TX (US); John Howard, College Station, TX (US); Richard Clough, College Station, TX (US); Kameshwari Pappu, College Station, TX (US)

(73) Assignees: Prodi Gene, Inc., College Station, TX (US); Geneucor International, Inc., Palo Alto, CA (US)

( * ) Notice: Subject to any disclaimer, the term of this patent is extended or adjusted under 35 U.S.C. 154(b) by 237 days.

(21) Appl. No.: 10/455,915

(22) Filed: Jun. 6, 2003

(65) Prior Publication Data

US 2004/0010820 A1    Jan. 15, 2004

Related U.S. Application Data

(60) Provisional application No. 60/387,700, filed on Jun. 11, 2002.

(51) Int. Cl.
| | |
|---|---|
| *A01H 5/00* | (2006.01) |
| *C12N 15/82* | (2006.01) |
| *C12N 15/87* | (2006.01) |
| *C12N 5/02* | (2006.01) |
| *C07H 21/04* | (2006.01) |

(52) U.S. Cl. .................. 800/320.1; 800/278; 800/287; 800/288; 800/294; 536/23.1; 435/412; 435/424; 435/430

(58) Field of Classification Search ................ 800/278, 800/288, 294, 320.1, 287; 536/23.1; 435/412, 435/424, 430
See application file for complete search history.

(56) References Cited

U.S. PATENT DOCUMENTS

| 6,002,068 A | 12/1999 | Privalle et al. ............. 800/289 |
| 6,278,041 B1 | 8/2001 | Lagrimini et al. .......... 800/279 |

FOREIGN PATENT DOCUMENTS

JP          152786       6/2000

OTHER PUBLICATIONS

Austin et. al. (Production and field performance of transgenic alfalfa (Medicago sativa L.) expressing α-amylase and manganese-dependent lignin peroxidase, Euphytica vol. 85, pp. 381-393, 1995.*
Webster's Dictionary, 1984, p. 1285 ).*
Hsiech et. al. Plant Physiology, v. 136, pp. 3427-3434, 2004).*
Buchanin, et al. Biochemistry & Molecular Biology of Plants (2000) American Society of Plant Physiologists, Rockville Md 20855, p. 1029, Table 19.2.*
Iturriaga et al. "Endoplasmic reticulum targeting and glycosylation of hybrid proteins in transgenic tabacco" The 1989, Plant Cell vol. 1 381-390.
Groover et al. "Secretion trap tagging of secreted and membrane-spanning proteins using Arabidopsis gene traps" Plant Physiology, 2003, vol. 132, 698-708.
Srinivasa et al. "Lignin Peroxidase and manganese peroxidase gene expression in wood" *American Chemical Society*, 207th ACS National Meeting, Mar. 13-17, 1994.
Austin et al, "Production and field performance of transgenic alfalfa (*Medicago sativa* L.) expressing alpha-amylase and manganese-dependent lignin peroxidase" *Euphytica* 85: 381-393 (1995).
Whitwam R. and Tien, M. "Heterologous expression and reconstitution of fungal Mn Peroxidase" *Archives of Biochemistry and Biophysics* vol. 333, No. 2 Sep. 15 pp. 439-446, 1996.
Mayfield et al., "Homologous expression of recombinant manganese peroxidase in *Phanerochaete chrysosporium*" *Applied and Environ. Microbiology* Dec. 1994, p. 4303-4309.
Stewart et al. "Efficient expression of a Phanerochaete chrysosporium manganese peroxides gene in *Aspergillus oryzae*" *Applied and Environ. Microbiology*, Mar. 1996, p. 860-864.
Gold et al. "Manganese Peroxidase" Chapter 17, Metal Ions in Biological Systems, pp. 559-596 (2000) Eds. Astric & Helmut, Mrcel Dekker pub.

* cited by examiner

*Primary Examiner*—Elizabeth McElwan
*Assistant Examiner*—Georgia Helmer
(74) *Attorney, Agent, or Firm*—Patricia A. Sweeney

(57) ABSTRACT

Expression of a recombinant manganese-dependent peroxidase in plants is described. Methods for the recovery of transgenic corn seeds that express high levels of functional manganese-dependent peroxidase are also provided. Manganese-dependent peroxidase vectors are engineered to contain sequences directing seed-preferred expression as well as sequences for cell wall-targeted localization.

23 Claims, 7 Drawing Sheets

Expression based on activity < 0.3 for all events

MPA, PGNpr6- Mn Peroxidase

COMMERCIAL PRODUCTION OF RECOMBINANT MANGANESE-DEPENDENT PEROXIDASE IN PLANTS

This application claims priority to U.S. Ser. No. 60/387,700, filed Jun. 11, 2002, which is incorporated by reference in its entirety.

FIELD OF THE INVENTION

The present invention relates to commercial production of heterologous proteins in plants. More specifically, the invention is to novel methods of overexpressing a heterologous, fungally-derived, manganese-dependent peroxidase in corn plants and to methods of targeting expression of manganese-dependent peroxidase to the cell wall of corn seeds. The present invention also relates to methods for the efficient recovery of fully active manganese-dependent peroxidase enzyme from corn seeds and to use of such proteins in commercial applications.

BACKGROUND OF THE INVENTION

Manganese-dependent peroxidases (or manganese peroxidases) are ligninolytic enzymes produced by white rot fungi. One such fungus is the basidiomycete *Phanerochaete chrysosporium* which is capable of degrading lignin to the point of mineralization with $H_2O$ and $CO_2$ as the final products. This degrading ability is due to the exocellular peroxidases such as various isozymes of lignin peroxidases (LiP) and manganese peroxidases (MnP) along with an extracellular $H_2O_2$-generating system. Manganese peroxidases are glycosylated heme protein peroxidases that catalyze the $H_2O_2$-dependent oxidation of $Mn^{2+}$ to $Mn^{3+}$. $Mn^{3+}$ is subsequently chelated by organic acids to create the diffusible oxidants that attack phenolic lignin structures (Kishi et al. 1994. Mechanism of manganese peroxidase compound II reduction. Effect of organic chelators and pH. *Biochemistry* 33: 8694–8701).

Several isozymes of manganese peroxidases from the fungus *Phanerochaete chrysosporium* have been described (Tien and Kirk. 1983. Lignin-degrading enzyme from the hymenomycete *Phanerochaete chrysosporium* Burds. *Science* 221: 661–663; Glenn et al. 1983. An extracellular $H_2O_2$-requiring enzyme preparation involved in lignin biodegradation by the white rot basidiomycete *Phanerochaete chrysosporium*. *Biochem. Biophys. Res. Commun.* 114: 1077–1083; Kuwahara et al. 1984. Separation and characterization of two extracellular $H_2O_2$-dependent oxidases from ligninolytic cultures of *Phanerochaete chrysosporium*. *FEBS Lett.* 169: 247–250) and the major isozyme, MnPI (H3) has been characterized in detail (Gold and Alic. 1993. Molecular biology of the lignin-degrading basidiomycete *Phanerochaete chrysosporium*. *Microbiol. Rev.* 57:605–622) and its X-ray structure reported (Sundaramoorthy, M., K. Kishi, M. H. Gold, and T. L. Poulos. 1994. The crystal structure of manganese peroxidase from *Phanerochaete chrysosporium* at 2.06-A resolution. *J Biol. Chem.* 269:32759–32767). These isozymes are encoded by a family of structurally related genes that are expressed under nutrient-limiting conditions during secondary metabolic growth phase of the fungus (Gettemy et al. 1998. Reverse transcription-PCR analysis of the regulation of the manganese peroxidase gene family. *Appl Environ Microbiol* 64(2): 569–74).

Commercial production of MnP enzymes has its application in the fields of paper making, waste treatment, bioremediation and others. In the pulp and paper industry, biological pulping and biological bleaching have the potential of improving the quality of pulp and paper, reducing energy costs and environmental pollution relative to traditional pulping and bleaching operations (U.S. Pat. No. 5,691,193). The technology has focused on white rot fungi that have complex extracellular ligninolytic enzymes such as MnP and LiP. Unlike the xylanases used in commercial bleaching to degrade hemicelluloses, peroxidases such as LiP and MnP have not been much tested in applications for manufacturing processes. This is simply due to the fact that effective methods for the production of commercially viable yields of enzyme have not been developed. Scale-up to industrial process requirements presents challenges that are difficult to simulate in the laboratory or pilot-scale tests. Thus there is a need in industry for large-scale production of ligninolytic enzymes such as MnP.

Large-scale production of MnP may also be employed in the treatment of environmental pollutants such as the cleanup of textile mill effluents as well as the bioremediation of dye-contaminated soil. For example, textile effluents cause a high environmental impact when released into the environment without correct treatment. Azo dyes are important synthetic compounds that are widely used in the dyestuff and textile industries. They are not biodegradable and tend to persist in the environment unless subjected to costly physical-chemical decontamination processes. Disperse Yellow 3 [2-(4'-acetamidophenylazo)-4-methylphenol] (DY3) which is an important yellow azo dye used in the industry, is a carcinogen. It was reported that the degradation of DY3 to $CO_2$ is possible by MnP (Spadaro and Renganathan. 1994. Peroxidase-catalyzed oxidation of azo dyes: mechanism of disperse Yellow 3 degradation. Arch Biochem Biophys. 312 (1): 301–307). Another example of environmental pollutants is the class of compounds called chlorophenols. 2,4,6,-Trichlorophenol and pentachlorophenol have been extensively used as wood preservatives and pesticides (Freiter. 1979. Chlorophenols, p 864–872. In "Encyclopedia of chemical technology". Mark, Othmer, Overberger and Seaborg (eds). Vol 5. John Wiley & Sons, Inc. New York, N.Y. and Rappe. 1980. Chloroaromatic compounds containing oxygen, phenols, diphenyl ethers, dibenzo-p-dioxins, and dibenzofuran, p 157–179. In Hutzinger (ed), The handbook for environmental chemistry. Springer-Verlag K G, Berlin, Germany). In addition, 2,4-dichlorophenol and 2,4,5-trichlorophenol are precursors in the synthesis of herbicides (Freiter, supra). It has been reported that the degradation of such persistant environmental pollutants by *Phanerochaete chrysosporium* involves an initial dechlorination step catalyzed by either LiP or MnP (Reddy et al. 1998. Degradation of 2,4,6-Trichlorophenol by *Phanerochaete chrysosporium*: Involvement of Reductive Dechlorination; Joshi and Gold. 1993. Degradation of 2,4,5-trichlorophenol by the lignin-degrading basidiomycete *Phanerochaete chrysosporium*. *Appl. Environ. Microbiol.* 59:1779–1785; and Valli and Gold. 1991. Degradation of 2,4-dichlorophenol by the lignin-degrading fungus *Phanerochaete chrysosporium*. *J. Bacteriol.* 173:345–352).

MnP can also be employed for bioremediation. For example, U.S. Pat. No. 6,268,204 describes how MnP is used to remediate liquid or solid waste streams containing organo-halides.

Fungal MnP is also capable of degrading aminonitrotoluenes, the main intermediates of the explosive 2,4,-trinitrotoluene (TNT). Radioactive experiments using a complex mixture of uniform ring-labeled 14C-TNT reduction products demonstrated the partial direct mineralization of these compounds by manganese peroxidase (Scheibner and Hofrichter. 1998. Conversion of aminonitrotoluenes by fungal manganese peroxidase. J Basic Microbiol. 38(1): 51–59).

MnP can also be employed in the synthesis of phenolic and aromatic amine polymers such as poly(p-ehylphenol) and poly(m-cresol) to help control product yields, molecular weight, molecular weight distribution and polydispersity (U.S. Pat. No. 6,096,859). Such polymers are important constituents of coatings, laminates and intergrated circuit chips. U.S. Pat. No. 5,608,040 reports a process for producing lignin-containing polymers in the presence of radical oxidizing enzymes such as MnP.

Several endeavors for over-expressing MnP in a variety of hosts have been reported. Attempts to express MnP genes in bacteria have resulted in the production of inclusion bodies containing catalytically inactive enzyme. The reason is that prokaryotic organisms such as bacteria inherently lack the ability to synthesize heme, a necessary component of the native enzyme (Andrawis et al. (eds) 1990. Biotechnology in Pulp and Paper Manufacture; Applications and Fundamental Investigations. Butterworth-Heinemann, Butterworth-Heinemann, Boston, 601). Efforts to optimize this system involved refolding of the inactive polypeptides into active enzyme under specific conditions (2 M urea, pH 8.0, in the presence of $CaCl_2$, hemin, and oxidized glutathione) (Whitwam and Tien. 1996. Heterologous expression and reconstitution of fungal Mn peroxidase. Arch Biochem Biophys 15; 333(2):439–46). Still, however, yields were low for large-scale commercial production.

Another system reported for MnP expression is the baculovirus expression system (Pease et al. 1991. Heterologous expression of active manganese peroxidase from *Phanerochaete chrysosporium* using the baculovirus expression system. Biochem. Biophys. Res. Commun. 179:897–903). This system is capable of producing biochemically active enzyme, indicating proper post-translational modifications, and enzymatic activity could be further enhanced (up to 15-fold increase) upon the addition of hemin at 1 ug/ml to the medium. Still, however, yields are not appreciably higher than those observed in *P. chrysosporium* cultures. The system also suffers from a serious limitation, its' high production costs. The addition of hemin to the medium is not a cost-effective measure since one gram of hemin crystals can cost about $27.

Expressing MnP in fungal systems also has its pitfalls. Attempts included the expression of exogenous sequences (heterologous expression) as well as the overexpression of endogenous MnP genes (homologous expression). Homologous expression of a recombinant MnP gene was attempted in *Phanerochaete chrysosporium*. An endogenous MnP gene was placed under the control of the glyceraldehyde-3-phosphate dehydrogenase promoter. Recombinant MnP yields were higher than those of the baculovirus expression systems. Heme insertion, folding, and secretion were normal (Mayfield et al. 1994. Homologous expression of recombinant manganese peroxidase in *Phanerochaete chrysosporium*. Appl Environ Microbiol. 60(12): 4303–9). Although the expression levels in this system were good enough for structural and functional studies of recombinant MnP, they were not high enough to support cost-effective large-scale industrial production.

Heterologous expression of recombinant MnP in the commercially available fungal systems, *Aspergillus oryzae* and *Aspergillus niger*, has also been attempted and shown to be possible. However, success was limited by poor yield and by the small fraction of peroxidase polypeptide that is assembled into a functional enzyme. In the *Aspergillus oryzae* system, MnP expression was attempted using a vector in which the cDNA of mnp-1 from *Phanerochaete chrysosporium* was fused with the *A. oryzae* Taka amylase promoter and secretion signal. Yields of 5 mg rMnP/L were obtained and optimal expression required 500 mg/L hemin in the medium. Lowered concentrations of hemin resulted in decreased yields (Stewart et al. 1996. Efficient expression of a *Phanerochaete chrysosporium* manganese peroxidase gene in *Aspergillus oryzae*. Appl. Environ. Microbiol. 62:860–864). In the *Aspergillus niger* system, overexpression of MnP was unsuccessful. Problems with this system included low specific activity of the recombinant MnP protein, low yields and degradation of a recombinant MnP: GLA fusion protein. The specific activity of rMnP was lower than that of the native enzyme. The initial yields obtained for rMnP in *A. niger* MGG029 were 5 to 10 mg/liter, which is low compared with other fungal proteins expressed in filamentous fungi. These yields could be increased to 100 mg of extracellular rMnP/liter under hemoglobin supplementation conditions (Conesa et al. 2000. Studies on the production of fungal peroxidases in *Aspergillus niger*. Appl Environ. Microbiol. 66(7): 3016–23).

The failure of genetically engineered bacterial or fungal systems to produce commercially high levels of MnP has prompted scientists to investigate the plant system. Transgenic plants offer the potential to be one of the most economical systems for large-scale production of proteins for industrial, pharmaceutical, veterinary and agricultural use. Advantages of plant systems include the low cost of growing a large biomass, easy scale-up (increase of planted acreage), natural storage organs (tubers, seeds), and established practices for efficient harvesting, transporting, storing and processing of the plant. Recombinant proteins can be targeted to seeds allowing stable storage of the recombinant proteins for extended periods. Plants offer advantages over other production systems since some proteins may be used without extensive purification, because for many applications, plant material is used directly as a food source or feed stock.

The only example attempting the expression of MnP in plants has failed. Austin et al. report that expressing the *P. chrysosporium* mnp-1 gene in alfalfa had deleterious effects on plant growth and development in vitro or in the greenhouse. Transgenic alfalfa plants were stunted and flowered later than control plants and the highest-expressing plants, with MnP levels above 0.3% soluble protein, died (Austin et al. 1995. Production and field performance of transgenic alfalfa (*Medicago sativa* L.) expressing alpha-amylase and manganese-dependent lignin peroxidase. Euphytica 85: 381–93).

The inventors have discovered that it is possible to obtain high level expression of a recombinant, fungally-derived nucleic acid sequence encoding MnP in corn seeds. It is, therefore, an object of the present invention to produce amounts of recombinant MnP (rMnP) that by far exceed the current capacity of traditional recombinant protein sources such as filamentous fungi or bacteria.

A further object of the invention is to produce MnP in plants such that the plant is viable, that is, lives to provide a source of MnP and does not die.

Another object of the invention is the application of large-scale production of MnP to industrial markets for which it had previously been economically unfeasible to enter.

Yet another object of the present invention is to produce rMnP in quantities large enough as to provide considerable cost savings for the industries.

An object of this invention is the development of a plant expression system that allows the efficient and large-scale production of heterologous proteins.

Another object of the invention is to preferentially express the rMnP in the seed of the plant.

A still further object of the invention is to direct expression of rMnP in plants to the cell wall of the plant.

An object of the invention is to further improve expression of rMnP in plants by backcrossing transgenic plants containing the MnP expressing gene into plants with good agronomic traits.

The objectives of this invention will become apparent in the description below. All references cited are incorporated herein by reference.

SUMMARY OF THE INVENTION

Transgenic corn plants and a process of obtaining them in which commercial levels of enzymatically active recombinant manganese peroxidase are produced are shown. Expression vectors are engineered to allow overexpression and accumulation of recombinant manganese peroxidase protein in plant tissue.

DETAILED DESCRIPTION OF THE PREFERRED EMBODIMENTS

Figure 1:
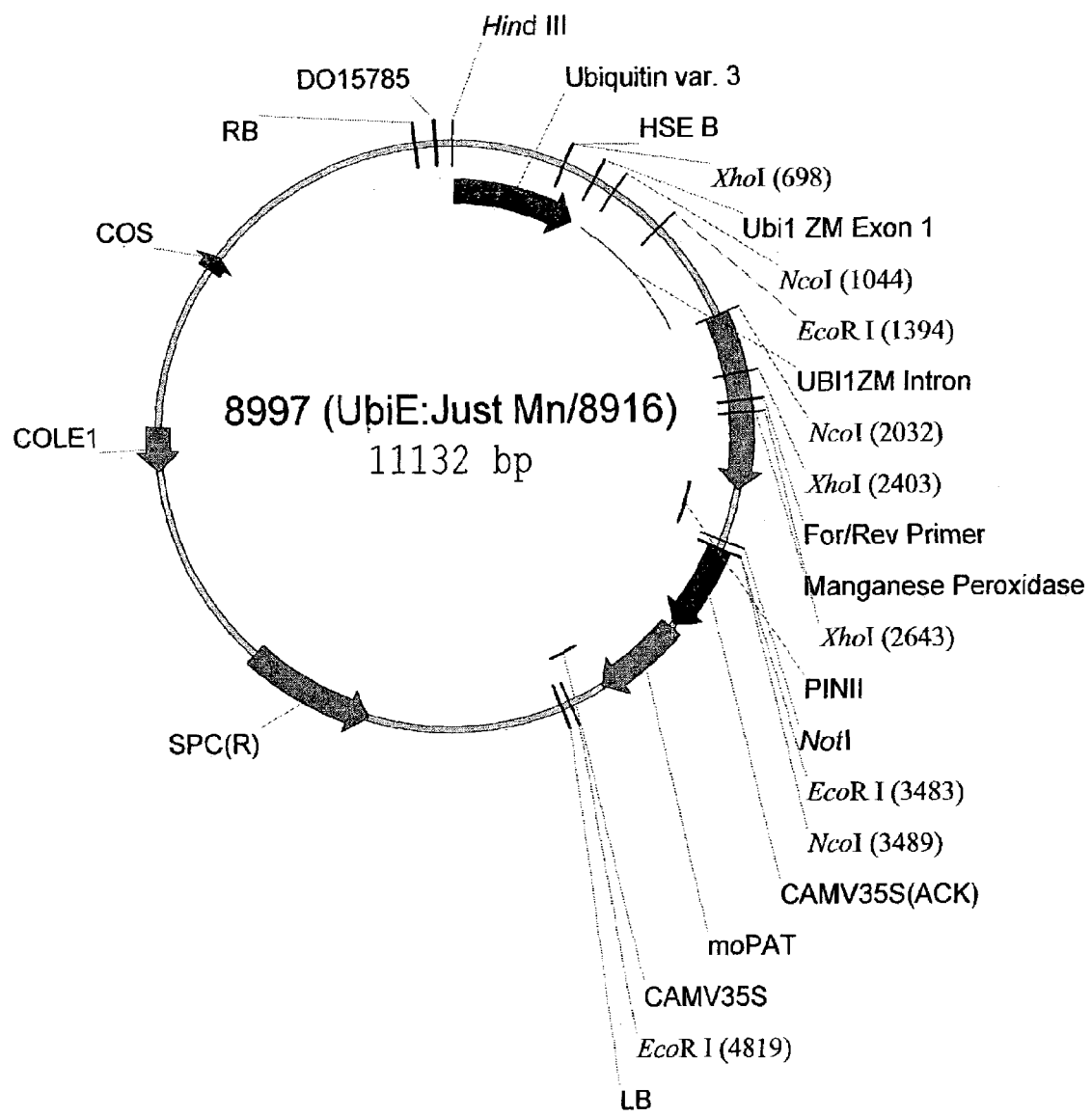
FIG. 1 is pPGN8997, a construct containing the manganese peroxidase gene, the PGNpr6 promoter, the moPAT marker (maize optimized PAT selectable marker) gene under the control of the CaMV 35S promoter.

The inventors have determined that expression of enzymatically active manganese peroxidase in plants is feasible and provides substantial advantages over the prior art attempts of producing the enzyme in microorganisms such as bacteria or fungi. According to the present invention, the levels of the enzyme produced in transgenic plants make it economically sound to produce commercial levels of the enzyme. Never before have such high commercially useful concentrations of the enzymes been obtained. Moreover, expression in plants has several advantages. Plants are more economical to grow and can be far more readily produced in large quantities than fungi. In addition, plant material is easy to store and transport.

While expression of manganese peroxidase at levels of about 1% total soluble protein in plant tissue are useful, expression levels of about 10% total soluble protein would allow for a very cost-effective system of commercial production of the MnP in plants.

According to the present invention, the secretion of MnP is a preferred method of expressing the protein at high levels. The inventors have determined that targeting the expression of MnP to the cell wall results in dramatic increases in the amount of MnP expressed in the plant which is correctly folded, and with active enzyme with heme incorporated.

In another preferred embodiment of the present invention, the MnP gene is linked to a promoter which preferentially expressed MnP to the seed of the plant. The inventors have discovered that directing the expression to the seed results in a further dramatic increase in protein accumulation and circumvents plant health problems throughout plant growth.

A combination of directing expression to the cell wall, and preferentially expressing MnP to the seed of the plant results in yet farther increases in expression levels. Expression in plants was typically about 0.5% of total soluble protein of the seed when the protein was expressed in the cytoplasm with a constitutive promoter. When expressed to the cell wall, a six-fold increase was observed. By combining both factors, expression levels up to 15% or a thirty-fold increase were observed.

In accordance with the present invention, a DNA molecule comprising a transformation/expression vector is engineered to incorporate a manganese peroxidase-encoding cDNA. There can be several isozymes for manganese peroxidase each encoded by a separate gene. Some examples are the mnp-1, mnp-2 and mnp-3 from *P. chrysosporium* (Pease et al. 1989. Manganese-dependent peroxidase from *Phanerochaete chrysosporium*. Primary structure deduced from cDNA sequence. *J. Biol. Chem.* 264:13531–35; Pribnow et al. 1989. Characterization of a cDNA encoding a manganese peroxidase, from the lignin-degrading basidiomycete *Phanerochaete chrysosporium*. *J. Biol. Chem.* 264: 5036–40; Pease and Tien. 1992. Heterogeneity and regulation of manganese peroxidases from *Phanerochaete chrysosporium*. *J Bacteriol.* 174(11): 3532–40); MnPL2 from *Pleurotus eryngii* (Ruiz-Duenas et al. 1999. Heterologous expression of *Pleurotus eryngii* peroxidase confirms its ability to oxidize $Mn^{2+}$ and different aromatic substrates. *Appli & Environ. Microbiol.* 65(10): 4705–07), mnp-2 from *Dichomitus squalens* (Li et al. 2001. Heterologous expression of a thermostable manganese peroxidase from *Dichomitus squalens* in *Phanerochaete chrysosporium*. *Arch Biochem Biophys.* 385(2): 348–56); and MnPI, MnPII and MnPIII from *Phanerochaete sordida* (Ruttimann-Johnson et al. 1994. Manganese peroxidases of the white rot fungus *Phanerochaete sordida*. *Appl. Environ. Microbiol.* 60(2): 599–605). The list of MnP genes here is not intended to be comprehensive but illustrative. The gene used in the present invention is from *P. chrysosporium*. The cDNA sequence is (SEQ ID NO: 1):

```
      A   V   C   P   D   G   T   R   V   T   N   A   A   C   A   F
  1 GCAGTCTGTC CAGACGGTAC CCGCGTCACC AACGCGGCGT GCTGCGCTTT
    CGTCAGACAG GTCTGCCATG GGCGCAGTGG TTGCGCCGCA CGACGCGAAA
      I   P   L   A   Q   D   L   Q   E   T   L   F   Q   G   D   C
 51 CATTCCGCTC GCACAGGACT TGCAAGAGAC TCTGTTCCAG GGTGACTGTG
    GTAAGGCGAG CGTGTCCTGA ACGTTCTCTG AGACAAGGTC CCACTGACAC
      G   E   D   A   H   E   V   I   R   L   T   F   H   D   A   I   A
101 GCGAAGATGC CCACGAAGTC ATCCGTCTGA CCTTCCACGA CGCTATTGCA
    CGCTTCTACG GGTGCTTCAG TAGGCAGACT GGAAGGTGCT GCGATAACGT
      I   S   Q   S   L   G   P   Q   A   G   G   A   D   G   S   M
151 ATCTCCCAGA GCCTAGGTCC TCAGGCTGGC GGCGGTGCTG ACGGCTCCAT
    TAGAGGGTCT CGGATCCAGG AGTCCGACCG CCGCCACGAC TGCCGAGGTA
      L   H   F   P   T   I   E   P   N   F   S   A   N   N   G   I
201 GCTGCACTTC CCGACAATCG AGCCCAACTT CTCCGCCAAC AACGGCATCG
    CGACGTGAAG GGCTGTTAGC TCGGGTTGAA GAGGCGGTTG TTGCCGTAGC
      D   D   S   V   N   N   L   P   F   M   Q   K   H   D   T   I
251 ATGACTCCGT CAACAACTTG CTTCCCTTCA TGCAGAAACA CGACACCATC
    TACTGAGGCA GTTGTTGAAC GAAGGGAAGT ACGTCTTTGT GCTGTGGTAG
      S   A   A   D   L   V   Q   F   A   G   A   V   A   L   S   N   C
301 AGTGCCGCCG ATCTTGTACA GTTCGCCGGT GCGGTCGCGC TGAGCAACTG
    TCACGGCGGC TAGAACATGT CAAGCGGCCA CGCCAGCGCG ACTCGTTGAC
      P   G   A   P   R   L   E   F   M   A   G   R   P   N   T   T
351 CCCAGGTGCT CCTCGCCTCG AGTTCATGGC TGGACGTCCG AACACTACCA
    GGGTCCACGA GGAGCGGAGC TCAAGTACCG ACCTGCAGGC TTGTGATGGT
      I   P   A   V   E   G   L   I   P   E   P   Q   D   S   V   T   K
401 TCCCCGCAGT TGAGGGCCTC ATTCCTGAGC CTCAAGACAG CGTCACCAAA
    AGGGGCGTCA ACTCCCGGAG TAAGGACTCG GAGTTCTGTC GCAGTGGTTT
      I   L   Q   R   F   E   D   A   G   N   F   S   P   F   E   V   V
451 ATCCTGCAGC GCTTCGAGGA CGCCGGCAAC TTCTCGCCGT TCGAGGTCGT
    TAGGACGTCG CGAAGCTCCT GCGGCCGTTG AAGAGCGGCA AGCTCCAGCA
      S   L   L   A   S   H   T   V   A   R   A   D   K   V   D   E
501 CTCGCTCCTG GCTTCACACA CCGTTGCTCG TGCGGACAAG GTCGACGAGA
    GAGCGAGGAC CGAAGTGTGT GGCAACGAGC ACGCCTGTTC CAGCTGCTCT
      T   I   D   A   A   P   F   D   S   T   P   F   T   F   D   T   Q
551 CCATCGATGC TGCGCCCTTC GACTCGACAC CCTTCACCTT CGACACCCAG
    GGTAGCTACG ACGCGGGAAG CTGAGCTGTG GGAAGTGGAA GCTGTGGGTC
      V   F   L   E   V   L   L   K   G   T   G   F   P   G   S   N   N
601 GTGTTCCTCG AGGTCCTGCT CAAGGGCACA GGCTTCCCGG GCTCGAACAA
    CACAAGGAGC TCCAGGACGA GTTCCCGTGT CCGAAGGGCC CGAGCTTGTT
      N   T   G   E   V   M   S   P   L   P   L   G   S   G   S   D
```

```
                                                    -continued
 651 CAACACCGGC GAGGTGATGT CGCCGCTCCC ACTCGGCAGC GGCAGCGACA

GTTGTGGCCG CTCCACTACA GCGGCGAGGG TGAGCCGTCG CCGTCGCTGT

T   G   E   M   R   L   Q   S   D   F   A   L   A   R   D   E   R

701 CGGGCGAGAT GCGCCTGCAG TCCGACTTTG CGCTCGCGCG CGACGAGCGC

GCCCGCTCTA CGCGGACGTC AGGCTGAAAC GCGAGCGCGC GCTGCTCGCG

T   A   C   F   W   Q   S   F   V   N   E   Q   E   F   M   A   A

751 ACGGCGTGCT TCTGGCAGTC GTTCGTCAAC GAGCAGGAGT TCATGGCGGC

TGCCGCACGA AGACCGTCAG CAAGCAGTTG CTCGTCCTCA AGTACCGCCG

S   F   K   A   A   M   K   L   A   I   L   G   H   S   R

801 GAGCTTCAAG GCCGCGATGG CGAAGCTCGC GATCCTCGGC CACAGCCGCA

CTCGAAGTTC CGGCGCTACC GCTTCGAGCG CTAGGAGCCG GTGTCGGCGT

S   S   L   I   D   C   S   D   V   V   P   V   P   K   P   A   V

851 GCAGCCTCAT CGACTGCAGC GACGTCGTCC CCGTCCCGAA GCCCGCCGTC

CGTCGGAGTA GCTGACGTCG CTGCAGCAGG GGCAGGGCTT CGGGCGGCAG

N   K   P   A   T   F   P   A   T   K   G   P   K   D   L   D   T

901 AACAAGCCCG CGACGTTCCC CGCGACGAAG GGCCCCAAGG ATCTCGACAC

TTGTTCGGGC GCTGCAAGGG GCGCTGCTTC CCGGGGTTCC TAGAGCTGTG

L   T   C   K   A   L   K   F   P   T   L   T   S   D   P   G

951 ACTCACGTGC AAGGCCCTCA AGTTCCCGAC GCTGACCTCT GACCCCGGTG

TGAGTGCACG TTCCGGGAGT TCAAGGGCTG CGACTGGAGA CTGGGGCCAC

A   T   E   T   L   I   P   H   C   S   N   G   G   M   S   C   P

1001 CTACCGAGAC CCTCATCCCC CACTGCTCCA ACGGCGGCAT GTCCTGCCCT

GATGGCTCTG GGAGTAGGGG GTGACGAGGT TGCCGCCGTA CAGGACGGGA

G   V   Q   F   D   G   P   A   .

1051 GGTGTTCAGT TCGATGGCCC TGCCTGA

CCACAAGTCA AGCTACCGGG ACGGACT
```

Although the present invention reports the expression of a MnP from *P. chrysosporium*, other homologous or substantially identical nucleic sequences are contemplated to be capable of being expressed in plants in the same manner. That is, the present invention contemplates any MnP-producing nucleic sequence.

In a preferred embodiment of the invention, expression of high levels of an active enzyme in the plant is accomplished by targeting the enzyme to the cell wall. This may be accomplished by the use of a signal sequence and in a preferred embodiment is the barley alpha amylase signal sequence (Rogers, J. C. 1985. Two barley alpha-amylase gene families are regulated differently in aleurone cells. *J. Biol. Chem.* 260: 3731–3738). The inventors have discovered that the use of such a localization sequence appears to aid in preventing the cytoplasmic accumulation of truncated forms of manganese peroxidase possibly resulting from pre-mature translation termination, proteolysis, or both.

The methods available for construction of recombinant genes comprising various modifications for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene is engineered to contain desired features, such as the desired localization sequences, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for manganese peroxidase; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In a preferred embodiment, the expression vector also contains a gene encoding a selection marker that is functionally linked to a promoter that controls transcription initiation. For a general description of plant expression vectors and reporter genes, see Gruber et al. 1993. "Vectors for Plant Transformation" in Methods of Plant Molecular Biology and Biotechnology. CRC Press. p 89–119. In a preferred embodiment, the selective gene is a glufosinate-resistance encoding DNA and in another preferred embodiment can be the phosphinothricin acetyl transferase ("PAT") or maize optimized PAT gene under the control of the CaMV 35S promoter. The gene confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

Promoter elements employed to control expression of MnP and the selection gene, respectively, can be any plant-compatible promoter. Those can be plant gene promoters, such as, for example, the ubiquitin promoter, the promoter for the small subunit of ribulose-1,5-bis-phosphate carboxylase, or promoters from the tumor-inducing plansmids from *Agrobacterium tumefaciens*, such as the nopaline synthase and octopine synthase promoters or viral promoters such as the cauliflower mosaic virus (CaMV) 19S and 35S promoters or the figwort mosaic virus 35S promoter. See Kay et al. 1987. Duplication of CaMV 35S promoter sequences creates a strong enhancer for plant genes. Science 236: 199–1302 and European patent application No. 0 342 926. See international application WO 91/19806 for a review of illustrative plant promoters suitably employed in the present invention. The range of available plant compatible promoters include tissue specific and inducible promoters. In one embodiment of the present invention, the manganese peroxidase DNA is under the transcriptional control of PGNpr6 promoter. (WO 01/94394). This is a ubiquitin-like promoter, lacking a heat shock element, the sequence of which is set forTH the below.

In a preferred embodiment, a tissue specific promoter is provided to direct transcription of the DNA preferentially to the seed. Use of such a sequence has been found to considerably increase the expression of MnP. One such promoter is the globulin promoter. This is the promoter of the maize globulin-1 gene, described by Belanger, F. C. and Kriz, A. L. 1991. Molecular Basis for Allelic Polymorphism of the maize Globulin-1 gene. *Genetics* 129: 863–972. It also can be found as accession number L22344 in the Genbank database. Another example is the phaseolin promoter. See, Bustos et al. 1989. Regulation of B-glucuronidase expression in transgenic tobacco plants by an A/T-rich cis-acting sequence found upstream of a french bean B-phaseolin gene. *The Plant Cell.* (1): 839–853.

Obviously, many variations on the promoters, selectable markers, signal sequences and other components of the construct are available to one skilled in the art.

In accordance with the present invention, a transgenic plant is produced that contains a DNA molecule, comprised of elements as described above, integrated into its genome so that the plant expresses a heterologous MnP-encoding DNA sequence. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al. 1993. "Procedures for Introducing Foreign DNA into Plants" in *Methods in Plant Molecular Biology and Biotechnology,* Glick et al (eds) CRC Press pp. 67–68 and by Phillips et al. 1988 "Cell/Tissue Culture and In Vitro Manipulation" in *Corn and Corn Improvement* 3d Edit. Sprague et al (eds) American Soc. of Agronomy pp. 345–387. The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al. 1992. *Bio/Technology* 10:26; and Weisinger et al. 1988. *Ann. Rev. Genet.* 22: 421–477. For example, the DNA construct maybe introduced into the genomic DNA of the plant cell using techniques such as microprojectile-mediated delivery (Klein et al. 1987. *Nature* 327: 70–73); electroporation (Fromm et al. 1985. *Proc. Natl. Acad. Sci.* 82: 5824); polyethylene glycol (PEG) precipitation (Paszkowski et al. 1984. *Embo J.* 3: 2717–272); direct gene transfer (WO 85/01856 and EP No. 0 275 069); in vitro protoplast transformation (U.S. Pat. No. 4,684,611) and microinjection of plant cell protoplasts or embryogenic callus (Crossway, 1985. *Mol. Gen. Genetics* 202:179–185). Co-cultivation of plant tissue with *Agrobacterium tumefaciens* is another option, where the DNA constructs are placed into a binary vector system (Ishida et al. 1996. "High Efficiency Transformation of Maize (*Zea mays* L.) Mediated by *Agrobacterium tumefaciens*". Nature Biotechnology 14:745–750). The virulence functions of the *Agrobacterium tumefaciens* host will direct the insertion of the construct into the plant cell DNA when the cell is infected by the bacteria. See, for example Horsch et al. 1984. Science 233: 496–498, and Fraley et al. 1983. Proc. Natl. Acad. Sci. 80: 4803.

Standard methods for transformation of canola are described by Moloney et al. 1989. "High Efficiency Transformation of *Brassica napus* Using Agrobacterium Vectors" *Plant Cell Reports* 8:238–242. Corn transformation is described by Fromm et al, 1990. Bio/Technology 8:833 and Gordon-Kamm et al, supra. *Agrobacterium* is primarily used in dicots, but certain monocots such as maize can be transformed by *Agrobacterium*. U.S. Pat. No. 5,550,318. Rice transformation is described by Hiei et al. 1994. "Efficient Transformation of Rice (*Oryza sativs* L.) Mediated by *Agrobacterium* and Sequence Analysis of the Boundaries of the T-DNA" The Plant Journal 6(2): 271–282, Christou et al. 1992. Trends in Biotechnology 10:239 and Lee et al. 1991. Proc. Nat'l Acad. Sci. USA 88:6389. Wheat can be transformed by techniques similar to those used for transforming corn or rice. Sorghum transformation is described by Casas et al., 1997. Transgenic sorghum plants obtained after microprojectile bombardment of immature inflorescences. In vitro cellular and developmental biology, Plant. 33:92–100 and by Wan et al. 1994. Plant Physiology. 104:37. Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the High II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in an *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the Ishida protocol as described provides for growing fresh culture of the *Agrobacterium* on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 and is preferably between 0.2 and 0.5. The bacteria are then centrifuged to remove the media and resuspended in the co-culture medium. Since Hi-II is used, medium preferred for Hi-II is used. This medium is described in considerable detail by Armstrong, C. I. and Green C. E. 1985. Establishment and maintenance of friable, embryogenic maize callus and involvement of L-proline. *Planta* 154:207–214. The resuspension medium is the same as that described above. All further Hi-II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is preferred to select the highest level of expression of MnP, and it is thus useful to ascertain expression levels in transformed plant cells, transgenic plants and tissue specific expression. One such method is to measure the expression of the target protein as a percentage of total soluble protein. One standard assay is the Bradford assay which is well known to those skilled in the art (Bradford, M. 1976. *Anal. Biochem.* 72:248). The biochemical activity of the recombinant protein should also be measured and compared with a wildtype standard. The activity of MnP can be determined by the methods described in Wariishi et al. 1992. Manganese (II) oxidation by manganese peroxidase from the basidiomycete *Phanerochaete chrysosporium*. Kinetic mechanism and role of chelators. *J. Biol. Chem.* 267:23688–23695.

The levels of expression of the gene of interest can be enhanced by the stable maintenance of a MnP encoding gene on a chromosome of the transgenic plant. Use of linked genes, with herbicide resistance in physical proximity to the MnP gene, would allow for maintaining selective pressure on the transgenic plant population and for those plants where the genes of interest are not lost.

Backcrossing methods may be used to introduce the gene into other plants. This is desirable when, for example, the gene is introduced into a plant hybrid, inbred, or variety that is easily transformed, but does not have good agronomic characteristics. Through backcrossing, the gene can be introduced into plants with good agronomic characteristics and/or characteristics that provide for better expression of the gene. This technique has been used for decades to introduce traits into a plant. An example of a description of this and other plant breeding methodologies that are well known can be found in references such as "Plant Breeding Methodology" edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

With transgenic plants according to the present invention, MnP can be produced in commercial quantities. Thus, the selection and propagation techniques described above yield a plurality of transgenic plants that are harvested in a conventional manner. The plant seed expressing the recombinant MnP can be used in a commercial process, or the MnP extracted. When using the seed itself, it can, for example, be made into flour and then applied in the commercial process. MnP extraction from biomass can be accomplished by known methods. Downstream processing for any production system refers to all unit operations after product synthesis, in this case protein production in transgenic seed (Kusnadi, A. R., Nikolov, Z. L., Howard, J. A., 1997. *Biotechnology and Bioengineering*. 56:473–484). Seed is processed either as whole seed ground into flour, or fractionated and the germ separated from the hulls and endosperm. If germ is used, it is usually defatted using a hexane extraction and the remaining crushed germ ground into a meal or flour. In some cases the germ is used directly in the industrial process or the protein can be extracted (See, e.g. WO 98/39461). Extraction is generally made into aqueous buffers at specific pH to enchance recombinant protein extraction and minimize native seed protein extraction. Subsequent protein concentration or purification can follow. In the case of industrial enzymes, concentration through membrane filtration is usually sufficient.

The enzyme can be used in a number of different industrial processes. Examples include bleaching of lignocellulosic kraft pulps by a process employing a sequential reaction of oxidative enzymes, such as MnP, and hydrogen peroxide. The process is described in U.S. Pat. No. 5,691,193. Briefly, it is a three step process that involves nonchlorine chemicals. The first step is the oxidation of kraft pulp with MnP in the presence of Mn(II) salts, chelator and hydrogen peroxide. The subsequent two steps comprise the chelation of metals in the pulp and alkaline hydrogen peroxide treatment. This use of MnP is an improvement over the current use of chlorine for depolymerization of lignin, which leads to the production of chlorinated aromatic compounds, which are an environmentally undesirable by-product of paper mills. MnP is also used for pulping processes. One example is given by U.S. Pat. No. 6,267,841 to a process of low energy thermomechanical pulping which employs treatment of the pulp with MnP between refining zones.

Another example lies in the field of bioremediation. Remediation of liquid or solid waste streams containing organo-halides is possible by a process described in U.S. Pat. No. 6,268,204. This process employs MnP to degrade halogenated aromatic compounds followed by forcing the products through a semi-permeable membrane partition.

Another use of MnP is in the synthesis of phenolic and aromatic amine polymers that are constituents of coatings, laminates and integrated circuit chips. Examples of such polymers include poly(p-ethylphenol) and poly(m-cresol). There is a need in the industrial synthesis of such compounds to control product yields, molecular weight, molecular weight distribution and polydispersity of the polymer molecules. U.S. Pat. No. 6,096,859 describes how such parameters may be controlled by a process employing peroxidases such as MnP. Another use for MnP in a manufacturing process is described in U.S. Pat. No. 5,608,040. The process is for producing lignin-containing polymers and comprises a polymerization step carried out in the presence of a radical oxidizing enzyme such as MnP. These are but few of the many uses to which the enzyme may be put.

The following illustrates, but is not intended to limit the scope of the invention. It will be evident to one skilled in the art that variations and modifications are possible and fall within the scope and spirit of the invention.

EXAMPLE 1

Preparation of Plasmids

In overview, seed from Hi-II maize kernels were transformed with constructs comprising elements according to the present invention. The constructs are designated pPGN8997, pPGN8998 and pPGN9037. The pPGN8997 construct comprises the PGNpr6 promoter, a MnP encoding sequence, PinII terminator sequences and the 35S promoter and terminator with moPAT (maize optimized PAT selectable marker). The pPGN8998 construct comprises the same elements as pPGN8997 except that the MnP encoding sequence has the barley alpha amylase export signal sequence. Construct pPGN9037 has the same elements as pPGN8998 except that the PGNpr6 promoter was substituted by the Globulin 1 promoter.

Figure 2:
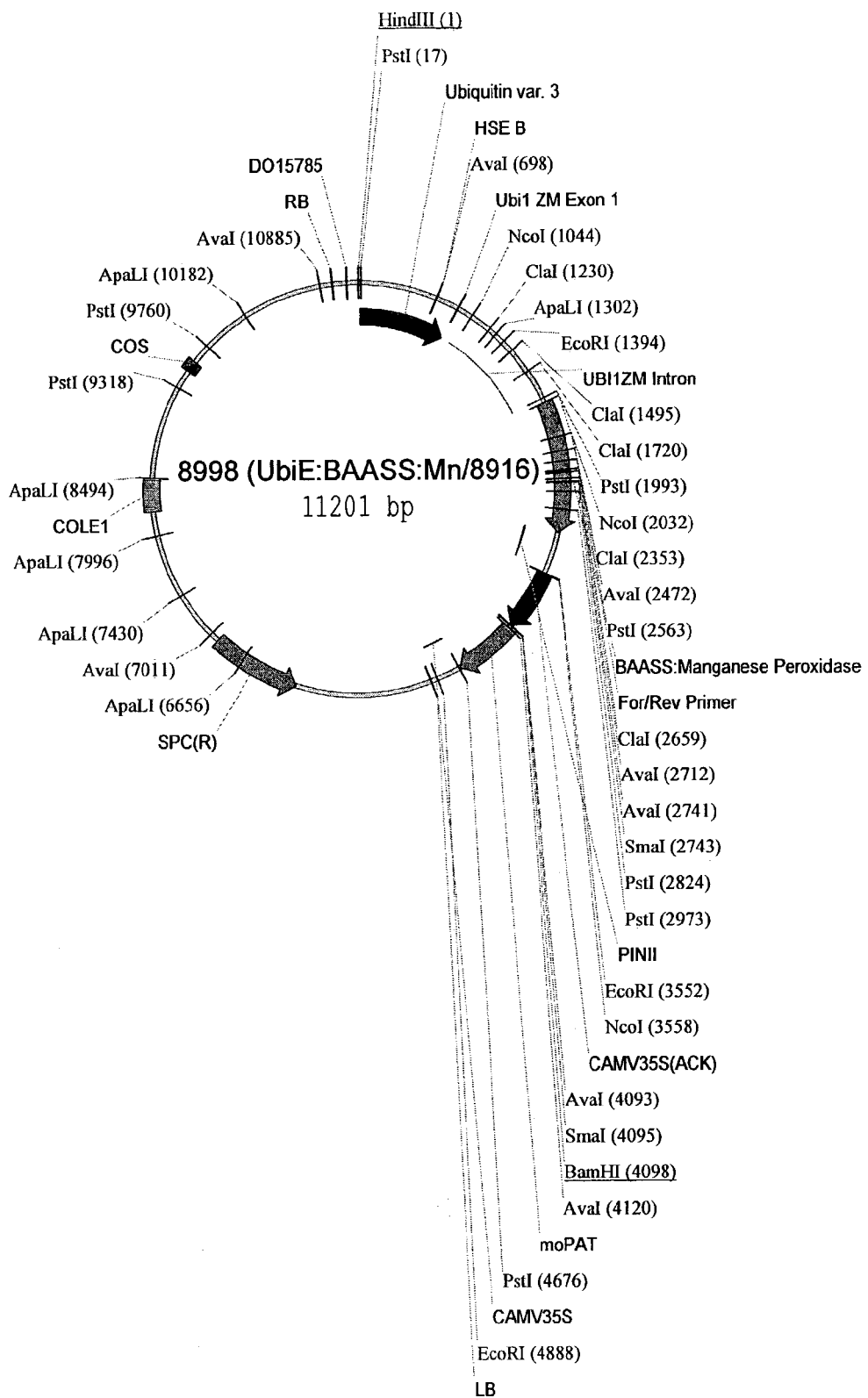
FIG. 2 is pPGN8998, which contains the same components as pPGN8997 but also contains the barley alpha-amylase signal sequence (BAASS).

A vector containing a cDNA for MnP and a fungal secretion signal has been described before; see Stewart et al. 1996. Efficient expression of a *Phanerochaete chrysosporium* manganese peroxidase gene in *Aspergillus olyzae*. *Appl. Environ. Microbiol.* 62:860–864. The secretion signal was either removed to give manganese peroxidase without a signal sequence in one case (pPGN8997-see FIG. 1) or replaced by the barley alpha amylase signal sequence (BAASS) in another case (pPGN8998-see FIG. 2). For the construction of pPGN8997 an NcoI restriction site containing the sequence necessary for the initiating methionine codon was added to the 5' end of the cDNA using polymerase chain reaction (PCR). This resulted in the MnP sequence without a signal sequence. For pPGN8998, the BAASS, which contains an NcoI site and the initiating methionine codon, was added to the 5' end of the cDNA using PCR resulting in a BAASS:manganese peroxidase construct. An HpaI restriction site was added to the 3' end of the cDNA using PCR. The resulting NcoI-HpaI fragments, either manganese peroxidase alone or BAASS:manganese peroxidase were ligated into the BbsI-HpaI vector fragment from pPGN2774 which contains the ubiquitin-like promoter and the Pin II terminator sequences resulting in plasmids K2686 or K2704 respectively. The HindIII-NcoI ubiquitin-like promoter fragment from both K2686 and K2704 were removed and replaced with the HindIII-NcoI fragment from pPGN7583 which contains the PGNpr6 promoter (WO 01/94394) resulting in K2792 and K2781 respectively. This modified ubiquitin-like promoter lacks a 5' heat shock sequence and is set forth below (SEQ ID NO: 2):

```
gtgcagcgtgaccggtcgtgccctctctagagataatgagcattgcatgtctaagttataaaaaattaccacatattttttttgtcaca cttgtttgaagtgcagtttatctatctttatacatatatttaaacttactctacgaataatataatctatagtactacaataatatcagtgtttta gagaatcatataaatgaacagttagacatggtctaaaggacaattgagtattttgacaacaggactctacagttttatctttttagtgtgc atgtgttctccttttttttttgcaaatagcttcacctatataatacttcatccattttattagtacatccatttagggtttagggttaatggttttttat agactaattttttttagtacatctattttattctattttagcctctaaattaagaaaactaaaactctattttagttttttttatttaataatttagatata aaatagaataaaataaagtgactaaaaattaaacaaataccctttaagaaattaaaaaaactaaggaaacattttttcttgtttcgagtag ataatgccagcctgttaaacgccgtcgacgagtctaacggacaccaaccagcgaaccagcagcgtcgcgtcgggccaagcgaa gcagacggcacggcatctctgtcgctgcctctcgagagttccgctccaccgttggacttgctccgctgtcggcatccagaaattgc gtggcggagcggcagacgtgagccggcacggcaggcggcctcctcctcctctcacggcacggcagctacgggggattcctttc ccaccgctccttcgctttcccttcctcgcccgccgtaataaatagacaccccctccacaccctctttccccaacctcgtgttgttcgga gcgcacacacacacaaccagatctcccccaaatccacccgtcggcacctccgcttcaaggtacgccgctcgtcctccccccccc ccctctctaccttctctagatcggcgttccggtccatggttagggccggtagttctacttctgttcatgtttgtgttagatccgtgtttgtg ttagatccgtgctgctagcgttcgtacacggatgcgacctgtacgtcagacacgttctgattgctaacttgccagtgtttctctttgggg aatcctgggatggctctagccgttccgcagacgggatcgatttcatgatttttttttgtttcgttgcatagggtttggtttgccctttttcctta tttcaatatatgccgtgcacttgtttgtcgggtcatcttttcatgctttttttgtcttggttgtgatgatgtggtctggttgggcggtcgttcta gatcggagtagaattctgtttcaaactacctggtggatttattaattttggatctgtatgtgtgtgccatacatattcatagttacgaattga agatgatggatggaaatatcgatctaggataggtatacatgttgatgcgggttttactgatgcatatacagagatgcttttttgttcgcttg
```

-continued

```
gttgtgatgatgtggtgtggttgggcggtcgttcattcgttctagatcggagtagaatactgtttcaaactacctggtgtatttattaatttt ggaactgtatgtgtgtgtcatacatcttcatagttacgagtttaagatggatggaaatatcgatctaggataggtatacatgttgatgtg ggttttactgatgcatatacatgatggcatatgcagcatctattcatatgctctaaccttgagtacctatctattataataaacaagtatgtt ttataattattttgatcttgatatacttggatgatggcatatgcagcagctatatgtggattttttagccctgccttcatacgctatttatttgc ttggtactgtttcttttgtcgatgctcaccctgttgtttggtgttacttctgca
```

Figure 3:
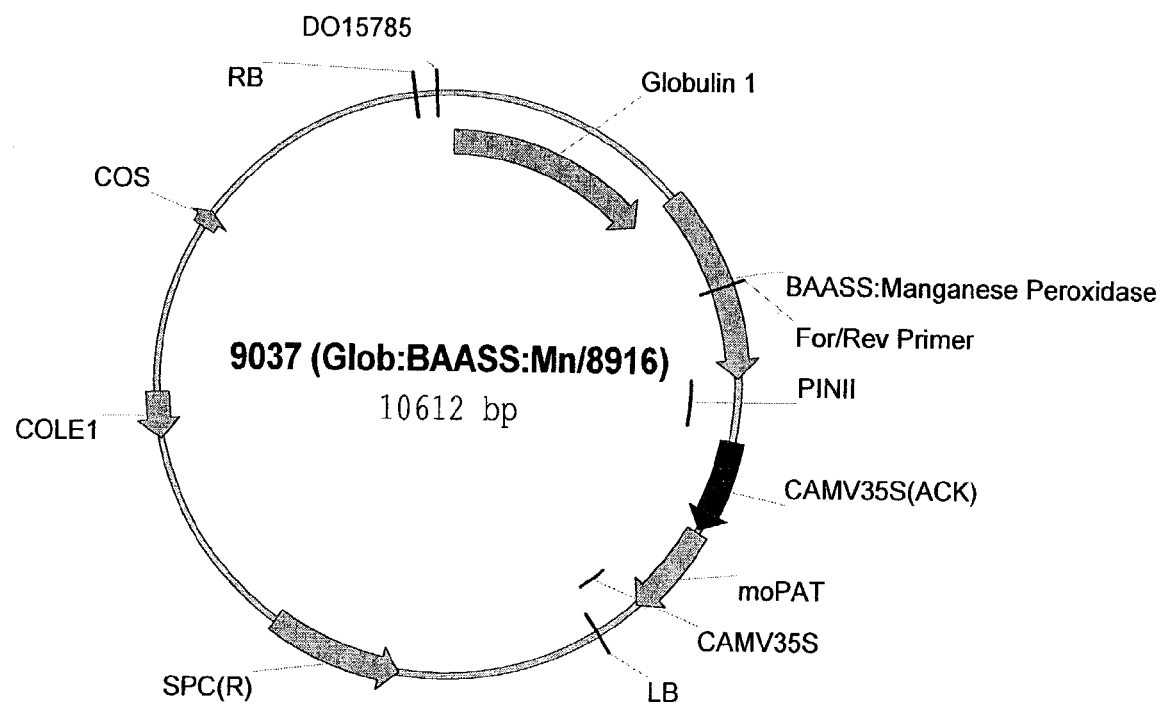
FIG. 3 is pPGN9037 which contains the same components as pPGN8998 except that the globulin 1 promoter is substituted for the PGNpr6 promoter.

The HindIII-NotI fragment from K2792 or K2781 was then ligated into the HindIII-Not vector PGN8916, which contains the 35S:PAT, resulting in PGN8997 (manganese peroxidase alone) or PGN8998 (BAASS:manganese peroxidase) respectively. To generate plasmid pPGN9037 (FIG. 3), the NcoI-NotI fragment from K2781 containing BAASS:manganese peroxidase along with the HindIII-NcoI fragment from KB381 containing the Globulin 1 promoter were ligated into the HindIII-NotI vector backbone from PGN8916 resulting in the final GlobulinI:BAASS:manganese peroxidase vector PGN9037. Constructs were sequenced to confirm that no errors were introduced during cloning procedures.

EXAMPLE 2

Transformation of Maize

Fresh immature zygotic embryos were harvested from Hi-II maize kernels at 1–2 mm in length. The general methods of *Agrobacterium* transformation were used as described by Japan Tobacco, at Ishida et al. 1996. "High efficiency transformation of maize (*Zea mays* L.) mediated by *Agrobacterium tumefaciens*" *Nature Biotechnology* 14:745–750 with the modifications described supra. Fresh embryos were treated with 0.5 ml log phase *Agrobacterium* strains EHA 101. Bacteria were grown overnight in a rich medium with kanamycin and spectinomycin to an optical density of 0.5 at 600 nm, pelleted, then re-inoculated in a fresh 10 ml culture. The bacteria were allowed to grow into log phase and were harvested at no more dense than OD600=0.5. The bacterial culture is resuspended in a co-culture medium.

For stable transformations, embryos were transferred to a bialaphos selective agent on embryogenic callus medium and transferred thereafter every two weeks to allow growth of transformed type II callus. Plants were regenerated from the callus. Those events resulting from the transformation of plants with the pPGN8997 vector are referred to as MPA events. Those resulting from pPGN8998 transformation are MPB events and those from pPGN9037 events are MPD events.

EXAMPLE 3

Manganese Peroxidase Analysis $T_1$ seeds of transgenic maize plants were analyzed by a MnP activity assay. Transgenic maize seed samples were homogenized individually with a custom seed pulverizer or in bulks of 50 seeds in a coffee grinder and extracted in 50 mM sodium tartrate pH 4.5. Protein concentration of the extracts was determined by the method of Bradford, with BSA as standard (Bradford, M. 1976. *Anal. Biochem.* 72:248). MnP activity in the extracts was measured by monitoring the oxidation of 2,6-dimethoxyphenol at 469 nm (Wariishi et al. 1992. Manganese(II) oxidation by manganese peroxidase from the basidiomycete *Phanerochaete chrysosporium*. Kinetic mechanism and role of chelators. *J. Biol. Chem.* 267: 23688–23695). Briefly, 0.2–10 microgram of seed extract was assayed at 28° C. for 5 minutes in 50 mM tartrate pH 4.5 containing 0.5 mM manganese sulfate, 1 mM 2,6-dimethoxphenol, and 0.05 mM hydrogen peroxide. Levels of MnP expressed in the extracts were reported as a percent of total soluble protein (% TSP).

Figure 4:
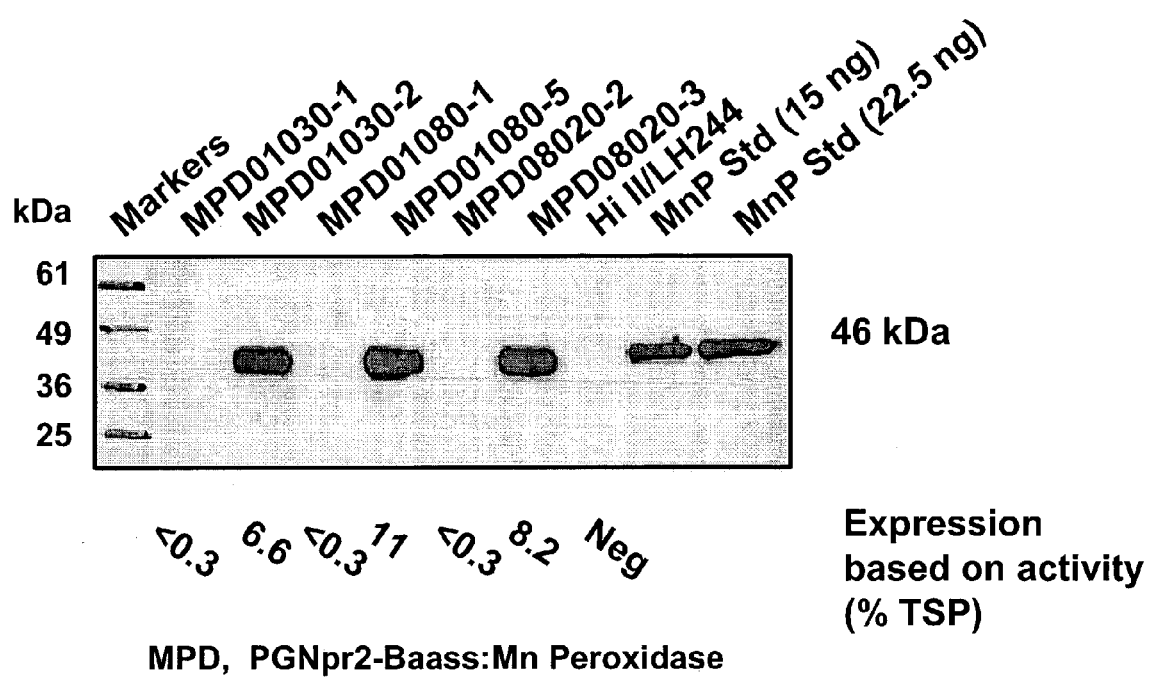
FIG. 4 shows a Western blot analysis of corn seed using manganese peroxidase specific antibodies. Seeds are from several $T_1$ MPD events and Hi-II/LH244 control corn. Blank lanes among MPD events reflect the expected expression ratio among $T_1$ seed resulting from outcross of the $T_0$ plants.

To test the expression of MnP in corn seed, protein extracts were prepared from individual $T_1$ seed of several MPD events and Hi-II/LH244 control corn. Using a manganese peroxidase-specific antibody, the full-length fungal enzyme was detected by immunoblot analysis for the transgenic individuals, while no product was seen in the control corn (see FIG. 4). Western analysis is a well known technique to those skilled in the art. This common procedure involves isolating the protein of interest and placing it on an acrylamide gel. The protein is then blotted onto a membrane and contacted with a labeling substance. See for example, Hood et al. 1997. Commercial Production of Avidin from Transgenic Maize; Characterization of Transformants, Production, Processing, Extraction and Purification. *Molecular Breeding* 3:291–306.

Figure 5:
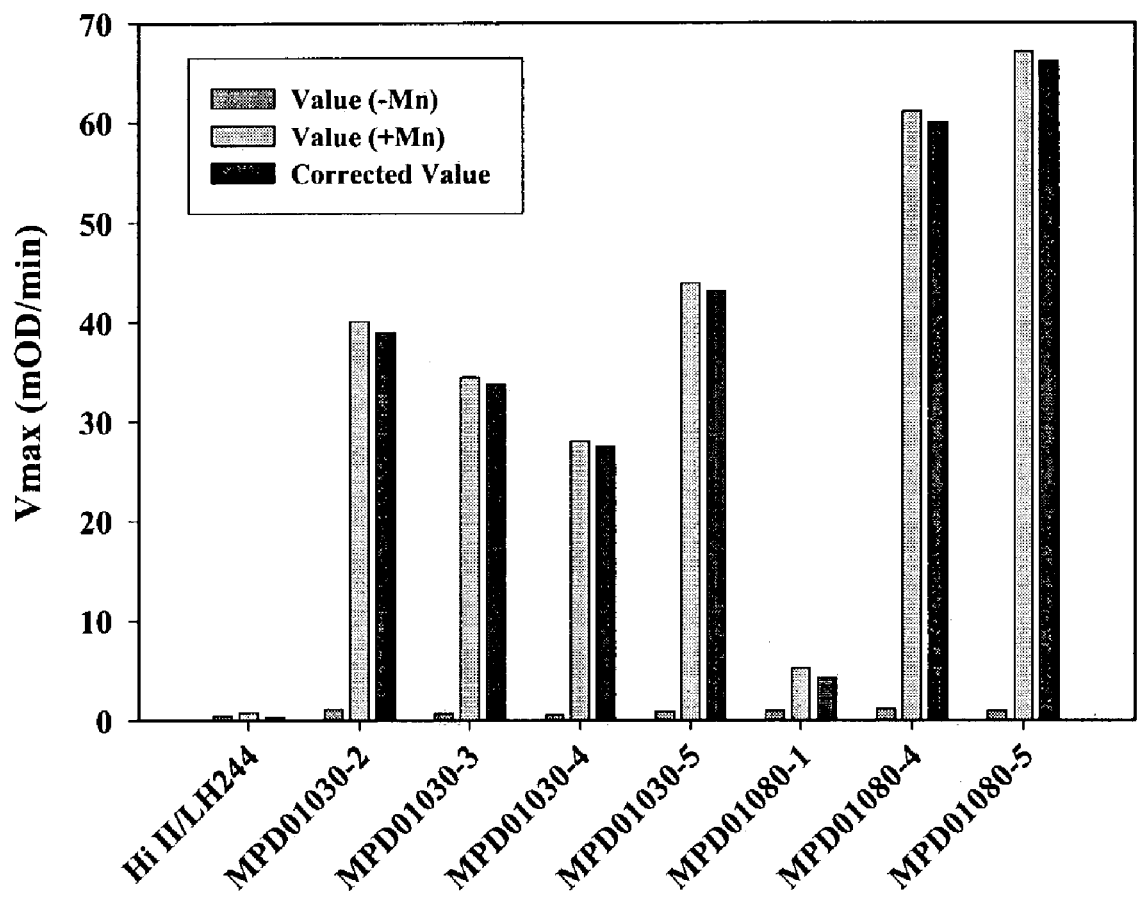
FIG. 5 is a graph showing enzymatic activity of rMnP from selected $T_1$ seeds from multiple MPD events and seeds from Hi-II/LH244 wildtype control plants.
Figure 6:
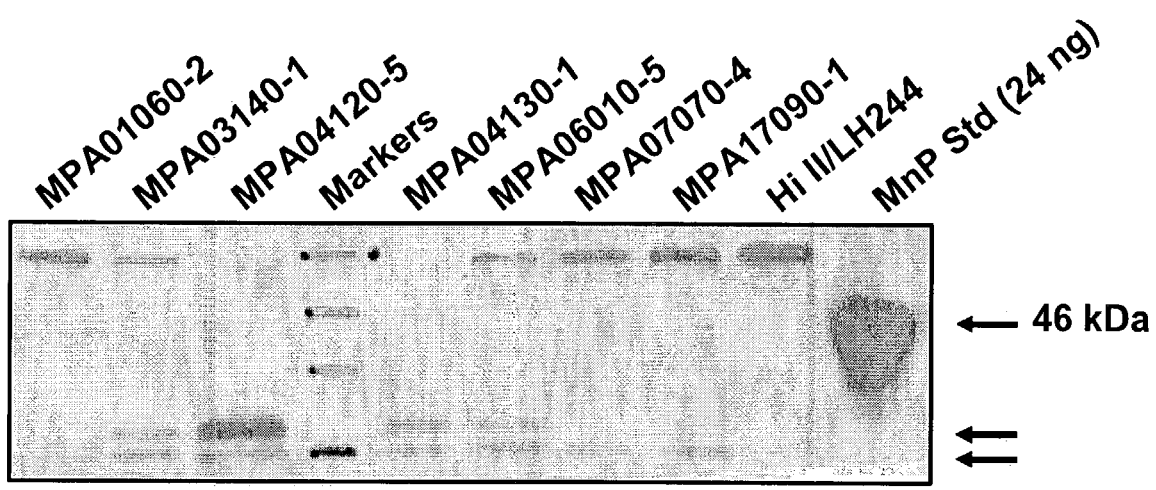
FIG. 6 is a Western blot analysis testing the expression of cytoplasmically targeted manganese peroxidase in seed samples from several MPA events.

To determine whether the recombinant MnP proteins were enzymatically active, extracts from $T_1$ seed transformed with the pPGN9037 construct (called MPD events) were analyzed by the methods of Wariishi, described supra. Compared to the Hi-II/LH244 (wildtype corn) control, a large increase in manganese-dependent enzyme activity was seen (FIG. 5), indicating that the heterologous MnP fungal enzyme was successfully expressed in corn seed. The inventors have found that protein extracts from seeds of MPA events (ie containing the pPGN9887 construct which does not have the BAASS signal sequence) had very low to negligible enzymatic activity (data not shown). Such extracts were further subjected to immunoblot analysis. Results (FIG. 6) indicate that none of the samples expressed detectable levels of full-length polypeptide. However, two smaller bands were detected. These bands likely represent truncated forms of MnP, possibly resulting from pre-mature translation termination, proteolysis, or both. This indicates that cytoplasmically-targeted MnP is truncated and that the secretion of MnP is a key element in successful overexpression and accumulation of enzymatically active protein.

Figure 7:
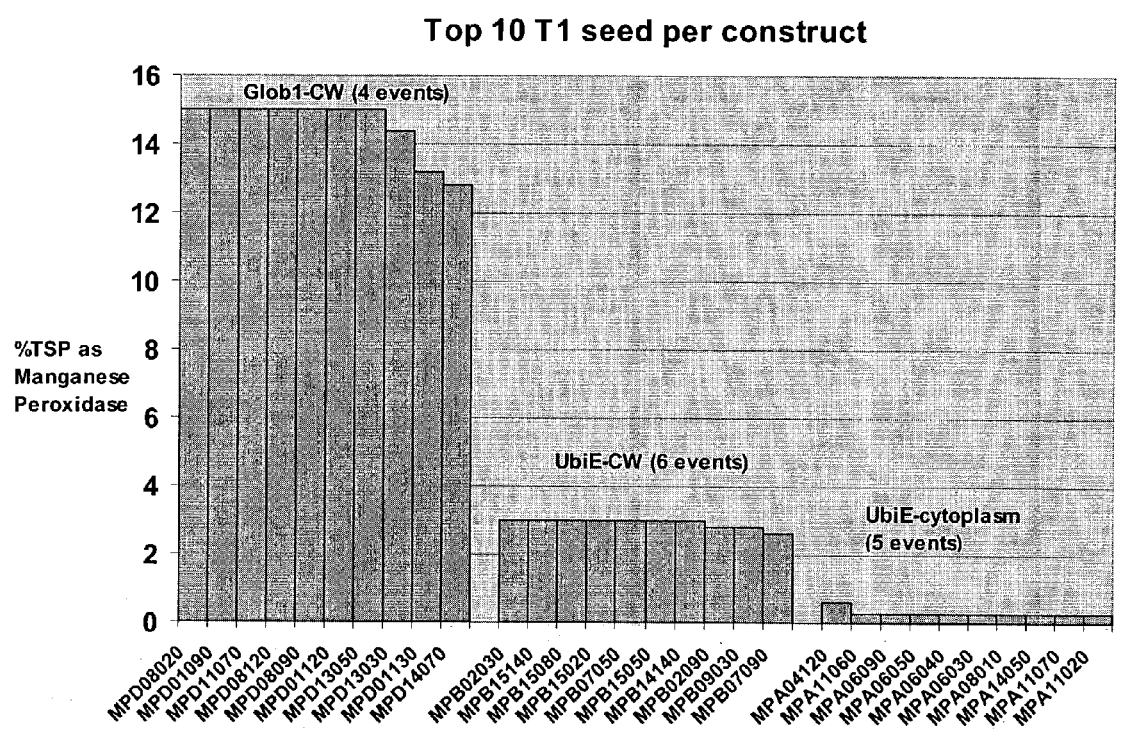
FIG. 7 is a graph showing the expression based on activity of manganese peroxidase in corn seeds resulting from multiple MPD, MPB and MPA events.

To compare the effects of different promoters and targeting on MnP accumulation in plant tissues, levels of MnP in seeds were determined as described, supra. Five individual seeds from ten different ears per transgenic event were analyzed and the highest single seed is reported for each plant. The highest single seed for constructs pPGN8997, pPGN8998 and pPGN9037 were plotted. As shown in FIG. 7, the highest-expressing seeds which had, on average, MnP levels at 15% TSP were from plants transformed with pPGN9037. Seeds from transgenic plants with pPGN8998 had MnP expression levels up to an average of 3% TSP and those from transgenic plants with pPGN8997 had MnP levels of less than 0.3% TSP. This clearly indicates that the secretion of the protein to the cell wall correlates with accumulation of high MnP levels. Preferential expression of the protein to the seed of the plant also results in increased MnP accumulation. It was found by the inventors that the use of a seed-preferred promoter (such as the Globulin 1 promoter) not only results in dramatic increases in accumulation over that of a constitutive promoter (such as PGNpr6 promoter), but also circumvents plant health problems observed throughout plant growth.

It is not necessary to extract the protein from the plant tissue, which instead can be used in direct application. Where it is extraction is desired, use of phosphate buffered saline with Tween (PBST) buffer is the default extraction method for initial screening of proteins, particularly when performing ELISA assays for quantification. However, for enzyme assays, the buffer is critical to enzyme activity detection, and PBST is not usually appropriate. Therefore, to improve quantification of the enzyme in corn seed extract, the seed was extracted in tartrate buffer, tartrate being one of the substrates of the manganese peroxidase enzyme. Estimates of recombinant protein yield per dry weight when proteins are extracted with PBST are approximately 100 fold less than their calculated percent of TSP. Tartrate buffer extracts four-fold less corn protein, though it has no effect on the solubility of the manganese peroxidase. Therefore, when MP is 15% of soluble protein in tartrate buffer, the estimate on a dry weight basis is approximately 0.0375%. (This is a single high seed value recovered several times in the T1 generation). Thus, particularly when using the tartrate buffer for extraction, improving expression levels even further through plant breeding techniques is desriable, as described below, is most useful.

EXAMPLE 4

Increasing Expression Levels Through Breeding

The Hi-II maize line that is used in tissue culture for plant transformation shows poor agronomic characteristics and is not high-yielding in the field. However, one of the most important goals for industrial protein production is yield near that of commercial corn lines. Thus, agronomic quality of early transgenic material can be improved through breeding the transgenic plant into plants with improved agronomic characteristics and/or which have chacteristics that provide for improved expression of the enzyme. To accomplish this, $T_1$ seed from selected high-MnP-expressing independent lines was planted in nurseries and crossed to elite inbreds. The goal is to develop high-yielding hybrids with good agronomic qualities. Improved expression levels are expected by breeding into elite varities using the backcrossing methods described, supra.

Crossing the Hi-II events with Stiff Stalk elite germplasm in particular can also increase event recovery. (See U.S. Ser. No. 10/349,392, to be published; Horn, Michael E.; Harkey, Robin L.; Vinas, Amanda K.; Drees, Carol F.; Barker, Donna K.; and Lane, Jeffrey R., "Use of Hill-Elite Hybrids in Agrobacterium-based Transformation of Maize" In Vitro Cell. Dev. Biol.-Plant. (In press)). Stiff Stalk inbreds have been available since at least about the 1950s and are derived from the Iowa Stiff Stalk synthetic population. Sprague, G. F. "Early testing of inbred lines of maize" J. Amer. Soc. Agron. (1946)38:108–117; for examples see PI accession no. 550481 and discussion of Stiff Stalk germplasm at U.S. Pat. Nos. 5,706,603; 6,252,148; 5,245,975; 6,344,599; 5,134,074; and Neuhausen, S. "A survey of Iowa Stiff Stalk parents derived inbreds and BSS(HT)C5 using RFLP analysis" MNL (1989)63: 110–111.

In this instance, the transgenic plant was crossed into one of two different elite Stiff Stalk elite plants, SP114 or SP112. Improved expression of MnP of ten times levels achieved in Hi-II is expected. In each generation, the highest expressing ears showing agronomic promise are selected and seed replanted from those ears in subsequent nurseries. After pollination, maturation and harvest, 50 seed from each progeny ear are combined, ground and analyzed for expression levels of extractable laccase. Only those showing improvement in the amount of MnP are selected for replanting. At each generation, approximately the top 10% of lines are replanted for the breeding program.

Levels of enzymatically active MnP that are produced in transgenic plants are commercially very attractive. Levels of 15% TSP are considerably higher than those obtained by conventional means. For example, such levels can allow the recovery of up to 0.04%–0.15% dry weight in a single $T_1$ seed and 0.02% dry weight in $T_2$ ear bulks. 0.15% dry weight is roughly equivalent to 1–5 g/L of enzyme produced in fungal fermentation. (see table below).

TABLE 1

Expression levels required to reach cost targets for industrial enzymes in fungal fermentation and corn seed expression systems.

| Cost/kg a.i. IE | Required expression level of industrial enzyme (IE) | |
|---|---|---|
|  | Fungal fermentation | Unpurified from corn seed |
| $1,000 | 1 g/L | 0.02% dry weight |
| $100 | 10 g/L | 0.2% dry weight |
| $10 | 100 g/L** | 2% dry weight |

**Not practical

Before this invention, the maximum amount of rMnP reported was 0.05–0.1 g/L in the Aspergillus niger expression system and at higher amounts, the fungi did not survive. Even under hemin supplementation conditions, this amount could only be increased to 0.1 g/L. Cost efficiency for purposes of commercial production indicates at least 1 g/L is preferable, equivalent to about 0.1% dry weight of total soluble protein in corn seed, or about 10% total soluble protein. While levels at about 0.01% of dry weight (about 1% total soluble protein) are useful, expression levels of 0.1% dry weight (about 10% total soluble protein) would be commercially attractive, as it would allow recovery of 1 g active ingredient from 1 kg of corn. Therefore, this invention allows the production of MnP amounts that far exceed the current capacity of traditional recombinant protein sources such as filamentous fungi or bacteria. Thus it is evident that the invention accomplishes at least all of its objectives.

What is claimed is:

1. A viable corn plant expressing manganese peroxidase, wherein the manganese peroxidase is preferentially directed to the cell wall of the plant.

2. Seeds of the plant of claim 1 expressing manganese peroxidase.

3. A Plant cells of a corn plant expressing manganese peroxidase such that the manganese peroxidase is preferentially directed to the cell wall and the plant cells is viable.

4. The plant of claim 1 wherein the manganese peroxidase is expressed at levels of at least about 0.1% total soluble protein.

5. The plant of claim 4 wherein the manganese peroxidase protein is expressed at levels of at least about 3.0% total soluble protein.

6. The plant of claim 5 wherein the manganese peroxidase protein is expressed at levels of at least about 10% total soluble protein.

7. The plant of claim 5 wherein the manganese peroxidase protein is expressed at levels of at least about 15% total soluble protein.

8. The plant of claim 1 further comprising a promoter preferentially directing expression of the manganese peroxidase to the seed of the plant.

9. A method for expressing manganese peroxidase in a viable corn plant comprising expressing in a corn plant cell a nucleic acid construct comprising a sequence encoding a manganese peroxidase protein, wherein the manganese peroxidase is preferentially directed to the cell wall.

10. The method of claim 9 further comprising operably linking with the nucleic acid construct a nucleotide sequence preferentially directing expression to the seed of the plant.

11. A method for producing increased levels of manganese peroxidase in a corn plants comprising:
  (i) expressing in a corn plant tissue a first nucleotide sequence encoding a manganese peroxidase protein and a second nucleotide sequence operably linked to the first nucleotide sequence and which preferentially directs expression of the first nucleotide sequence to the cell wall of the plant tissue;
  (ii) culturing a plant from the plant tissue;
  (iii) growing and harvesting the plant such that manganese peroxidase is expressed.

12. The method of claim 11 further comprising a third nucleotide sequence preferentially directing expression of the first nucleotide sequence to the seed of the plant.

13. The method of claim 11 wherein the manganese peroxidase is expressed at levels of at least about 0.1% total soluble protein or more.

14. The method of claim 13 wherein the manganese peroxidase is expressed at levels of at least about 3% total soluble protein or more.

15. The method of claim 14 wherein the manganese peroxidase is expressed at levels of at least about 10% total soluble protein or more.

16. A method of producing manganese peroxidase at levels of at least about 0.1% total soluble protein, comprising providing biomass from a plurality of corn plants, of which at least certain plants contain a nucleotide molecule comprising a heterologous nucleotide sequence coding for the manganese peroxidase, wherein the nucleotide sequence is operably linked to a nucleotide sequence preferentially directing of the manganese peroxidase to the cell wall of the certain plants to produce manganese peroxidase expressed at levels of at least about 0.1% total soluble protein.

17. The plant of claim 1 expressing manganese peroxidase at levels of at least 0.3% total soluble protein.

18. The method of claim 9 comprising expressing manganese peroxidase at levels of at least about 0.1% total soluble protein in said plant.

19. The method of claim 9 comprising expressing manganese peroxidase at levels of at least about 0.3% total soluble protein in said plant.

20. The method of claim 9 comprising expressing manganese peroxidase at levels of at least about 1% total soluble protein in said plant.

21. The method of claim 9 comprising expressing manganese peroxidase at levels of at least about 3% total soluble protein.

22. The method of claim 9 comprising expressing manganese peroxidase at levels of at least about 10% total soluble protein.

23. The method of claim 9 comprising expressing manganese peroxidase at levels of at least about 15% total soluble protein.

* * * * *

SEQUENCE LISTING

<160> NUMBER OF SEQ ID NOS: 3

<210> SEQ ID NO 1
<211> LENGTH: 1077
<212> TYPE: DNA
<213> ORGANISM: Phanerochaete chrysosporium

```
<220> FEATURE:
<221> NAME/KEY: CDS
<222> LOCATION: (1)..(1074)

<400> SEQUENCE: 1 gca gtc tgt cca gac ggt acc cgc gtc acc aac gcg gcg tgc tgc gct    48
Ala Val Cys Pro Asp Gly Thr Arg Val Thr Asn Ala Ala Cys Cys Ala
  1               5                  10                  15 ttc att ccg ctc gca cag gac ttg caa gag act ctg ttc cag ggt gac    96
Phe Ile Pro Leu Ala Gln Asp Leu Gln Glu Thr Leu Phe Gln Gly Asp
             20                  25                  30 tgt ggc gaa gat gcc cac gaa gtc atc cgt ctg acc ttc cac gac gct   144
Cys Gly Glu Asp Ala His Glu Val Ile Arg Leu Thr Phe His Asp Ala
         35                  40                  45 att gca atc tcc cag agc cta ggt cct cag gct ggc ggc ggt gct gac   192
Ile Ala Ile Ser Gln Ser Leu Gly Pro Gln Ala Gly Gly Gly Ala Asp
 50                  55                  60 ggc tcc atg ctg cac ttc ccg aca atc gag ccc aac ttc tcc gcc aac   240
Gly Ser Met Leu His Phe Pro Thr Ile Glu Pro Asn Phe Ser Ala Asn
 65                  70                  75                  80 aac ggc atc gat gac tcc gtc aac aac ttg ctt ccc ttc atg cag aaa   288
Asn Gly Ile Asp Asp Ser Val Asn Asn Leu Leu Pro Phe Met Gln Lys
                 85                  90                  95 cac gac acc atc agt gcc gcc gat ctt gta cag ttc gcc ggt gcg gtc   336
His Asp Thr Ile Ser Ala Ala Asp Leu Val Gln Phe Ala Gly Ala Val
            100                 105                 110 gcg ctg agc aac tgc cca ggt gct cct cgc ctc gag ttc atg gct gga   384
Ala Leu Ser Asn Cys Pro Gly Ala Pro Arg Leu Glu Phe Met Ala Gly
        115                 120                 125 cgt ccg aac act acc atc ccc gca gtt gag ggc ctc att cct gag cct   432
Arg Pro Asn Thr Thr Ile Pro Ala Val Glu Gly Leu Ile Pro Glu Pro
    130                 135                 140 caa gac agc gtc acc aaa atc ctg cag cgc ttc gag gac gcc ggc aac   480
Gln Asp Ser Val Thr Lys Ile Leu Gln Arg Phe Glu Asp Ala Gly Asn
145                 150                 155                 160 ttc tcg ccg ttc gag gtc gtc tcg ctc ctg gct tca cac acc gtt gct   528
Phe Ser Pro Phe Glu Val Val Ser Leu Leu Ala Ser His Thr Val Ala
                165                 170                 175 cgt gcg gac aag gtc gac gag acc atc gat gct gcg ccc ttc gac tcg   576
Arg Ala Asp Lys Val Asp Glu Thr Ile Asp Ala Ala Pro Phe Asp Ser
            180                 185                 190 aca ccc ttc acc ttc gac acc cag gtg ttc ctc gag gtc ctg ctc aag   624
Thr Pro Phe Thr Phe Asp Thr Gln Val Phe Leu Glu Val Leu Leu Lys
        195                 200                 205 ggc aca ggc ttc ccg ggc tcg aac aac aac acc ggc gag gtg atg tcg   672
Gly Thr Gly Phe Pro Gly Ser Asn Asn Asn Thr Gly Glu Val Met Ser
    210                 215                 220 ccg ctc cca ctc ggc agc ggc agc gac acg ggc gag atg cgc ctg cag   720
Pro Leu Pro Leu Gly Ser Gly Ser Asp Thr Gly Glu Met Arg Leu Gln
225                 230                 235                 240 tcc gac ttt gcg ctc gcg cgc gac gag cgc acg gcg tgc ttc tgg cag   768
Ser Asp Phe Ala Leu Ala Arg Asp Glu Arg Thr Ala Cys Phe Trp Gln
                245                 250                 255 tcg ttc gtc aac gag cag gag ttc atg gcg gcg agc ttc aag gcc gcg   816
Ser Phe Val Asn Glu Gln Glu Phe Met Ala Ala Ser Phe Lys Ala Ala
            260                 265                 270 atg gcg aag ctc gcg atc ctc ggc cac agc cgc agc agc ctc atc gac   864
Met Ala Lys Leu Ala Ile Leu Gly His Ser Arg Ser Ser Leu Ile Asp
        275                 280                 285 tgc agc gac gtc gtc ccc gtc ccg aag ccc gcc gtc aac aag ccc gcg   912
```

| | | | | | | | | | | | | | |
|---|---|---|---|---|---|---|---|---|---|---|---|---|---|
|Cys|Ser|Asp|Val|Val|Pro|Val|Pro|Lys|Pro|Ala|Val|Asn|Lys|Pro|Ala|
| |290| | | |295| | | |300| | | | | | acg ttc ccc gcg acg aag ggc ccc aag gat ctc gac aca ctc acg tgc    960
Thr Phe Pro Ala Thr Lys Gly Pro Lys Asp Leu Asp Thr Leu Thr Cys
305                 310                 315                 320 aag gcc ctc aag ttc ccg acg ctg acc tct gac ccc ggt gct acc gag   1008
Lys Ala Leu Lys Phe Pro Thr Leu Thr Ser Asp Pro Gly Ala Thr Glu
            325                 330                 335 acc ctc atc ccc cac tgc tcc aac ggc ggc atg tcc tgc cct ggt gtt   1056
Thr Leu Ile Pro His Cys Ser Asn Gly Gly Met Ser Cys Pro Gly Val
                340                 345                 350 cag ttc gat ggc cct gcc tga                                       1077
Gln Phe Asp Gly Pro Ala
        355

<210> SEQ ID NO 2
<211> LENGTH: 1976
<212> TYPE: DNA
<213> ORGANISM: Artificial Sequence
<220> FEATURE:
<223> OTHER INFORMATION: Description of Artificial Sequence: Synthetic
      DNA sequence

<400> SEQUENCE: 2
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aaatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg    300 caaatagctt cacctatata atacttcatc cattttatta gtacatccat ttagggttta    360
gggttaatgg ttttttataga ctaattttttt tagtacatct attttattct attttagcct    420
ctaaattaag aaaactaaaa ctctatttta gttttttttat ttaataattt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctcgagagtt ccgctccacc gttggacttg ctccgctgtc    720
ggcatccaga aattgcgtgg cggagcggca gacgtgagcc ggcacggcag gcggcctcct    780
cctcctctca cggcacggca gctacggggg attccttttcc caccgctcct tcgctttccc    840
ttcctcgccc gccgtaataa atagacaccc cctccacacc ctctttcccc aacctcgtgt    900
tgttcggagc gcacacacac acaaccagat ctcccccaaa tccacccgtc ggcacctccg    960
cttcaaggta cgccgctcgt cctcccccccc ccccctctc taccttctct agatcggcgt   1020
tccggtccat ggttagggcc cggtagttct acttctgttc atgtttgtgt tagatccgtg   1080
tttgtgttag atccgtgctg ctagcgttcg tacacggatg cgacctgtac gtcagacacg   1140
ttctgattgc taacttgcca gtgtttctct ttggggaatc ctgggatggc tctagccgtt   1200
ccgcagacgg gatcgatttc atgatttttt ttgtttcgtt gcataggggtt tggtttgccc   1260 tttttccttta tttcaatata tgccgtgcac ttgtttgtcg ggtcatcttt tcatgctttt   1320
ttttgtcttg gttgtgatga tgtggtctgg ttgggcggtc gttctagatc ggagtagaat   1380
tctgtttcaa actacctggt ggattttatta attttggatc tgtatgtgtg tgccatacat   1440
attcatagtt acgaattgaa gatgatggat ggaaatatcg atctaggata ggtatacatg   1500

-continued

```
ttgatgcggg ttttactgat gcatatacag agatgctttt tgttcgcttg gttgtgatga   1560
tgtggtgtgg ttgggcggtc gttcattcgt tctagatcgg agtagaatac tgtttcaaac   1620
tacctggtgt atttattaat tttggaactg tatgtgtgtg tcatacatct tcatagttac   1680
gagtttaaga tggatggaaa tatcgatcta ggataggtat acatgttgat gtgggtttta   1740
ctgatgcata tacatgatgg catatgcagc atctattcat atgctctaac cttgagtacc   1800
tatctattat aataaacaag tatgttttat aattattttg atcttgatat acttggatga   1860
tggcatatgc agcagctata tgtggatttt tttagccctg ccttcatacg ctatttattt   1920
gcttggtact gtttcttttg tcgatgctca ccctgttgtt tggtgttact tctgca       1976
```

<210> SEQ ID NO 3
<211> LENGTH: 358
<212> TYPE: PRT
<213> ORGANISM: Phanerochaete chrysosporium

<400> SEQUENCE: 3

```
Ala Val Cys Pro Asp Gly Thr Arg Val Thr Asn Ala Ala Cys Cys Ala
  1               5                  10                  15

Phe Ile Pro Leu Ala Gln Asp Leu Gln Glu Thr Leu Phe Gln Gly Asp
                 20                  25                  30

Cys Gly Glu Asp Ala His Glu Val Ile Arg Leu Thr Phe His Asp Ala
             35                  40                  45

Ile Ala Ile Ser Gln Ser Leu Gly Pro Gln Ala Gly Gly Gly Ala Asp
         50                  55                  60

Gly Ser Met Leu His Phe Pro Thr Ile Glu Pro Asn Phe Ser Ala Asn
 65                  70                  75                  80

Asn Gly Ile Asp Asp Ser Val Asn Asn Leu Leu Pro Phe Met Gln Lys
                 85                  90                  95

His Asp Thr Ile Ser Ala Ala Asp Leu Val Gln Phe Ala Gly Ala Val
                100                 105                 110

Ala Leu Ser Asn Cys Pro Gly Ala Pro Arg Leu Glu Phe Met Ala Gly
            115                 120                 125

Arg Pro Asn Thr Thr Ile Pro Ala Val Glu Gly Leu Ile Pro Glu Pro
        130                 135                 140

Gln Asp Ser Val Thr Lys Ile Leu Gln Arg Phe Glu Asp Ala Gly Asn
145                 150                 155                 160

Phe Ser Pro Phe Glu Val Val Ser Leu Leu Ala Ser His Thr Val Ala
                165                 170                 175

Arg Ala Asp Lys Val Asp Glu Thr Ile Asp Ala Ala Pro Phe Asp Ser
            180                 185                 190

Thr Pro Phe Thr Phe Asp Thr Gln Val Phe Leu Glu Val Leu Leu Lys
        195                 200                 205

Gly Thr Gly Phe Pro Gly Ser Asn Asn Asn Thr Gly Glu Val Met Ser
    210                 215                 220

Pro Leu Pro Leu Gly Ser Gly Ser Asp Thr Gly Glu Met Arg Leu Gln
225                 230                 235                 240

Ser Asp Phe Ala Leu Ala Arg Asp Glu Arg Thr Ala Cys Phe Trp Gln
                245                 250                 255

Ser Phe Val Asn Glu Gln Glu Phe Met Ala Ala Ser Phe Lys Ala Ala
            260                 265                 270

Met Ala Lys Leu Ala Ile Leu Gly His Ser Arg Ser Ser Leu Ile Asp
        275                 280                 285
```

-continued

```
Cys Ser Asp Val Val Pro Val Pro Lys Pro Ala Val Asn Lys Pro Ala
    290                 295                 300

Thr Phe Pro Ala Thr Lys Gly Pro Lys Asp Leu Asp Thr Leu Thr Cys
305                 310                 315                 320

Lys Ala Leu Lys Phe Pro Thr Leu Thr Ser Asp Pro Gly Ala Thr Glu
                325                 330                 335

Thr Leu Ile Pro His Cys Ser Asn Gly Gly Met Ser Cys Pro Gly Val
            340                 345                 350

Gln Phe Asp Gly Pro Ala
        355
```